(12) United States Patent
Gey (10) Patent No.: US 10,188,478 B2
(45) Date of Patent: Jan. 29, 2019

(54) DEVICE HOUSING PROTECTED AGAINST PENETRATION OF LIQUIDS

(75) Inventor: Michael Gey, Lübeck (DE)

(73) Assignee: DRÄGERWERK AG & CO. KGAA, Lübeck (DE)

( * ) Notice: Subject to any disclaimer, the term of this patent is extended or adjusted under 35 U.S.C. 154(b) by 832 days.

(21) Appl. No.: 13/618,160

(22) Filed: Sep. 14, 2012

(65) Prior Publication Data

US 2013/0119840 A1 May 16, 2013

(30) Foreign Application Priority Data

Nov. 16, 2011 (DE) .................. 10 2011 055 411

(51) Int. Cl.
| A61B 50/00 | (2016.01) |
| A61B 50/30 | (2016.01) |
| H02G 3/08  | (2006.01) |

(52) U.S. Cl.
CPC ............. *A61B 50/30* (2016.02); *H02G 3/088* (2013.01); *A61B 2050/0066* (2016.02)

(58) Field of Classification Search
CPC .. H02G 5/04; H02G 9/04; H02G 3/088; F24F 13/22; F24F 13/222; G06F 1/1656; H02B 1/066; A61B 50/30; A61B 2050/0066
USPC ......... 312/229, 228, 232, 265.6, 223.2, 100, 312/101
See application file for complete search history.

(56) References Cited

U.S. PATENT DOCUMENTS

| 4,381,063 A * | 4/1983 | Leong .................... 220/242 |
| 4,620,061 A * | 10/1986 | Appleton ................ 174/51 |
| 7,086,409 B2 * | 8/2006 | Robinson ................. 137/1 |
| 2004/0123997 A1 * | 7/2004 | Drane et al. .............. 174/67 |
| 2004/0222007 A1 * | 11/2004 | Nakamrura ............. 174/65 G |
| 2006/0249296 A1 | 11/2006 | Drane et al. |
| 2007/0215614 A1 * | 9/2007 | Matsui ..................... 220/3.2 |
| 2010/0046158 A1 * | 2/2010 | Nakatani et al. ....... 361/679.33 |
| 2010/0163568 A1 * | 7/2010 | Mucci et al. ............ 220/796 |
| 2011/0154889 A1 * | 6/2011 | Stafford et al. .......... 73/61.59 |
| 2011/0304248 A1 * | 12/2011 | Oota ......................... 312/229 |
| 2012/0035447 A1 * | 2/2012 | Frey et al. ................ 600/365 |
| 2012/0111597 A1 * | 5/2012 | Korcz et al. .............. 174/67 |
| 2012/0272830 A1 * | 11/2012 | Gugerli ..................... 99/295 |

FOREIGN PATENT DOCUMENTS

| CN | 2696080 Y | 4/2005 |
| CN | 200973215 Y | 11/2007 |
| WO | WO 2011073310 A2 * | 6/2011 |

\* cited by examiner

*Primary Examiner* — Daniel J Troy
*Assistant Examiner* — Hiwot E Tefera
(74) *Attorney, Agent, or Firm* — McGlew and Tuttle, P.C.

(57) ABSTRACT

A housing (1) for devices with at least one module, which is to be protected against penetration of liquids, has at least one cover (2) that is arranged on the top side of the housing (1). A simple and cost-effective production and maintenance is provided by the outer edge areas (4) of the cover (2) having at least one collar (5, 7, 9, 11), which protrudes downwards when cover (2) is closed and has a preferably circumferential drip edge (12). The housing (1) is provided in the edge area of an opening (13) to be closed by the cover (2) with at least one mounting groove (15), which, when the cover (2) is closed, is arranged below the at least one collar (7, 11), such that a liquid dripping from the drip edge (12) falls into the mounting groove (15).

20 Claims, 7 Drawing Sheets

DEVICE HOUSING PROTECTED AGAINST PENETRATION OF LIQUIDS

CROSS REFERENCE TO RELATED APPLICATIONS

This application claims the benefit of priority under 35 U.S.C. § 119 of German Patent Application DE 10 2011 055 411.4 filed Nov. 16, 2011, the entire contents of which are incorporated herein by reference.

FIELD OF THE INVENTION

The present invention pertains to a housing for devices with at least one module, which is to be protected against penetration of liquids, and with at least one cover arranged on the top side of the housing.

BACKGROUND OF THE INVENTION

Especially in the area of medical engineering, a large number of devices are used which contain sensitive modules, which may not come into contact with liquids, especially moisture, because otherwise dysfunctions or functional failure is to be feared. However, particularly also when using medical engineering devices, there is an increased risk that liquids are spilled and reach the device housing. Here, the liquid can especially reach the interior through the gaps of covers on the top side of the housing. For this reason, flaps and covers, which make access to the device interior possible for operation and maintenance, are usually arranged essentially vertically on the lateral outer walls. In essentially horizontally arranged covers on the housing top side, seals can be used to prevent a penetration of liquid into the device interior. Housings with such seals are expensive to produce and maintain for the seals must be tested routinely for tightness and possibly be lubricated or replaced with new ones.

SUMMARY OF THE INVENTION

An object of the present invention is to provide a housing of the type mentioned in the introduction with at least one cover arranged on the housing top side, which can be produced cost-effectively and causes only low maintenance costs.

The present invention accomplishes this object by at least one collar being arranged in an outer edge area of the cover, which protrudes downwards when the cover is closed and has a drip edge, by the housing being provided in the edge area of an opening to be closed by the cover with at least one mounting groove, which is arranged below the at least one collar when the cover is closed, such that a liquid dripping from the drip edge falls into the mounting groove. Thus, the present invention dispenses with preventing the penetration of liquids by means of a seal. A liquid applied to the top side of the housing can penetrate through gaps between the cover and the housing and thus reach the mounting groove, which prevents the further flowing of the liquid into the housing interior and as a result protects the sensitive modules against the liquid.

An especially practical embodiment of the present invention provides that two collars are arranged at a distance to one another and protrude downwards into the mounting groove. This measure effectively prevents a surge of liquid from passing through the mounting groove from the outside to the inside because of a velocity of the liquid and prevents the liquid from reaching the housing area to be protected on the inside, because the two collars protruding into the mounting groove stand in the way of the liquid surge and slow it down, such that the slowed-down liquid is finally held back in the mounting groove and flows off in a controlled manner.

In a preferred embodiment a gap formed between the outside of the collar and the housing has a gap width (gap), at which an adherence of liquid is prevented as a result of capillary forces. If this gap is designed as too narrow, then liquid continues to adhere therein and does not reach the mounting groove. From a sufficient width of approx. 1 mm to 2 mm or more, the capillary effects are no longer able to hold the liquid at the viscosities mainly occurring, which liquid then drips over the drip edge into the mounting groove. The gap width should not be too large for aesthetic reasons and therefore should not exceed 4 mm maximum.

Further, a gap of less than 4 mm has the advantage that a too rapid penetration of the liquid and a resulting unchecked crossing of the receiving channel in a direction transverse to the flow direction can be prevented. With a gap between 1 mm and 4 mm it is also advantageous if two collars, at a distance to each other, are arranged to project downwardly into the receiving channel. It is thereby achieved that drip quantities that could, at an inclination of the equipment, overcome the outer collar to penetrate into the apparatus, due to the surface tension at the underside of the lid, instead drain off at the latest at the inner collar into the receiving channel.

In an embodiment of the present invention, provisions are made for the or each mounting groove to have at least one end, through which penetrated liquid is guided out of the housing. In this way, it is guaranteed that the liquid collecting in the housing can run out of the mounting groove not inwards, but only outwards. This measure also makes the operation of the device easier, since a removal of the penetrated liquid is not necessary.

When the end projects laterally over a housing wall, the liquid is prevented from running outside along the housing wall and perhaps still penetrates through a gap in the housing positioned further below. In this embodiment, the liquid drips from the end at a distance from the housing wall.

The present invention is also improved by the mounting groove being designed as inclined towards the end. Consequently, the running of the liquid in the direction of the end is made easier and the end velocity is increased. Depending on how sharply the mounting groove inclines, the penetrated liquid can, under the circumstances, nevertheless, still flow with a slight inclination of the housing.

However, even when a flowing of the liquid should not be possible because of absent or clogged end or because of sharper tilting of the housing, a variant of the present invention, in which the or each mounting groove can receive a liquid volume of at least 100 mL, preferably more than 200 mL, without liquid reaching the modules to be protected in the interior of the housing, proves to be advantageous.

In another advantageous embodiment of the present invention, the or each mounting groove has an inner wall lying below the closed cover, from which the inside of the nearest (in case of two collars of the inner-lying one running at a distance to one another) collar of the cover is spaced apart so far that an adherence of liquid between the inner wall of the mounting groove and inside of the collar is prevented as a result of capillary forces. As in the external gap, a distance of at least 1 mm, and preferably 2 mm or more is necessary here to guarantee a dripping off of the liquid at the viscosities of the usually occurring liquids.

An especially high safety against penetration of liquid from the cover or from the mounting groove is obtained when the upper edge of the inner wall of the mounting groove is higher than the lower edge of the collar of the cover. In this embodiment, the inner wall of the mounting groove can at the same time also be used for mounting the cover on the housing by placing the cover on its upper edge.

The present invention is also improved by the measure that the or each mounting groove has a rounded profile with inner radius sufficient for an easy cleaning. Such a rounded profile prevents inner-lying edges, in which dirt might deposit, which is then difficult to remove. Furthermore, the mounting groove is easy to clean, when it is wide enough to make possible the access for a usual cleaning brush or a cleaning rag wound around the finger of a cleaning person to the bottom of the mounting groove. On the other hand, it must also be deep enough to receive a sufficiently large volume of liquid and to be able to hold back a liquid surge. A mounting groove is best suitable for these tasks when its inner radii are greater than 3 mm (R3—German standard DIN 250 and SAE J517 TYPE 100 R3 STANDARD), preferably even greater than 5 mm (R5—German standard DIN 250 and SAE J517 TYPE 100 R5 STANDARD), its depth is greater than 5 mm and its width is greater than 10 mm.

The mounting groove designed according to the present invention and the collar cooperating with it with drip edge of the cover are thus easy to clean and otherwise maintenance-free. Moreover, the production of a device housing designed according to the present invention is more cost-effective than in devices, whose cover is protected by means of a hermetic seal against the penetration of liquids. One merit of the present invention is to have recognized that a hermetic seal is not needed to keep liquids reaching the housing away from the sensitive modules of the device and to handle the components, which can be reached by opening the cover, are to be maintained or are removable or are to be used, in a simple, clean and hygienic manner. Because of the gap between the collar of the cover and the walls of the mounting groove according to the present invention, a creep barrier is obtained against capillary moisture transport. Furthermore, the design of the housing according to the present invention makes possible not only a more cost-effective production with relatively high production tolerances and simple assembly, but also the embodiment of an attractive design.

Exemplary embodiments of the present invention are described in detail below on the basis of the drawings. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
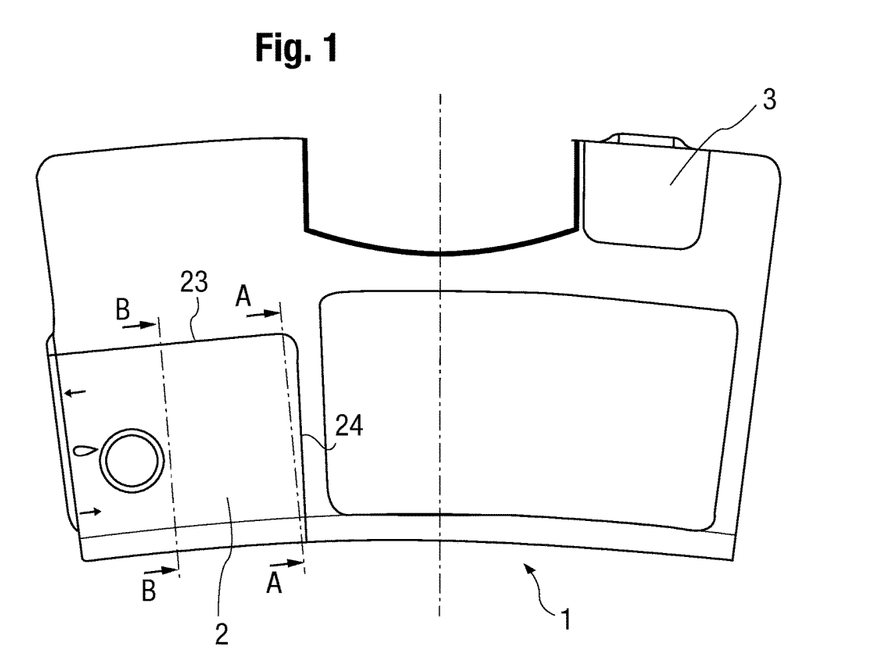
FIG. 1 is a top view of a device housing according to the present invention with two covers.

Referring to the drawings in particular, the housing 1 shown in FIG. 1 of a medical device has a first large cover 2 and a second, small cover 3, which each protect a (not shown) module against the penetration of liquids. On the other hand, the covers 2, 3 make possible the simple and unhindered access to the modules placed in the housing 1, especially for maintenance purposes.

Figure 4:
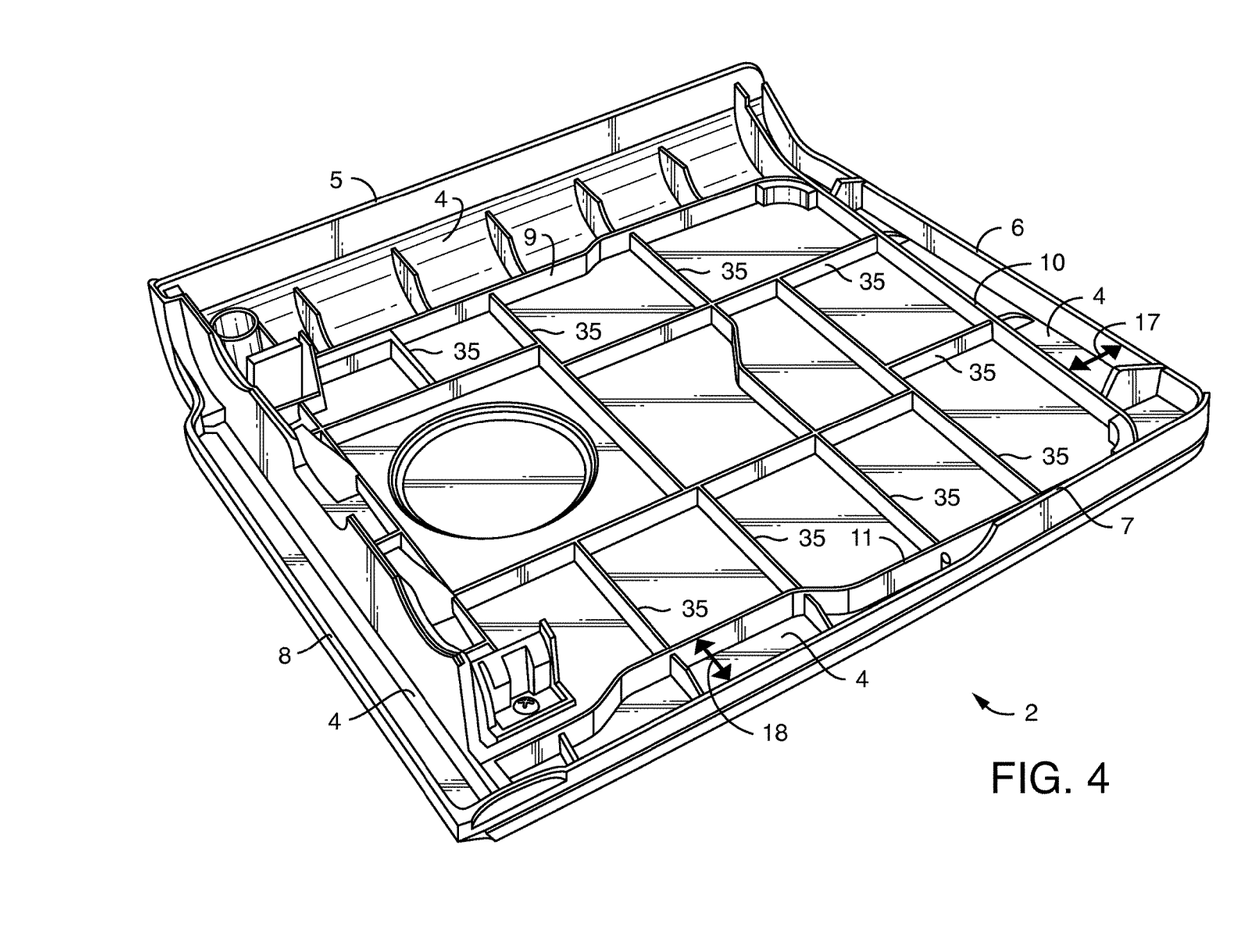
FIG. 4 is a perspective view of the bottom side of a first cover of the housing of FIG. 1 according to the present invention.

As is best seen in FIG. 4, the first cover has, at its outer edge area 4, a circumferential outer collar 5, 6, 7, 8, which consists of the four sections 5 through 8. Furthermore, the first cover 2 has an inner collar 9, 10, 11, which, just as outer collar 5, 6, 7, 8, protrudes downwards when the cover is closed, whereby the collars 5 through 11 have each a lower drip edge 12, at which any liquid present can drip, see FIG. 2.

Figure 5:
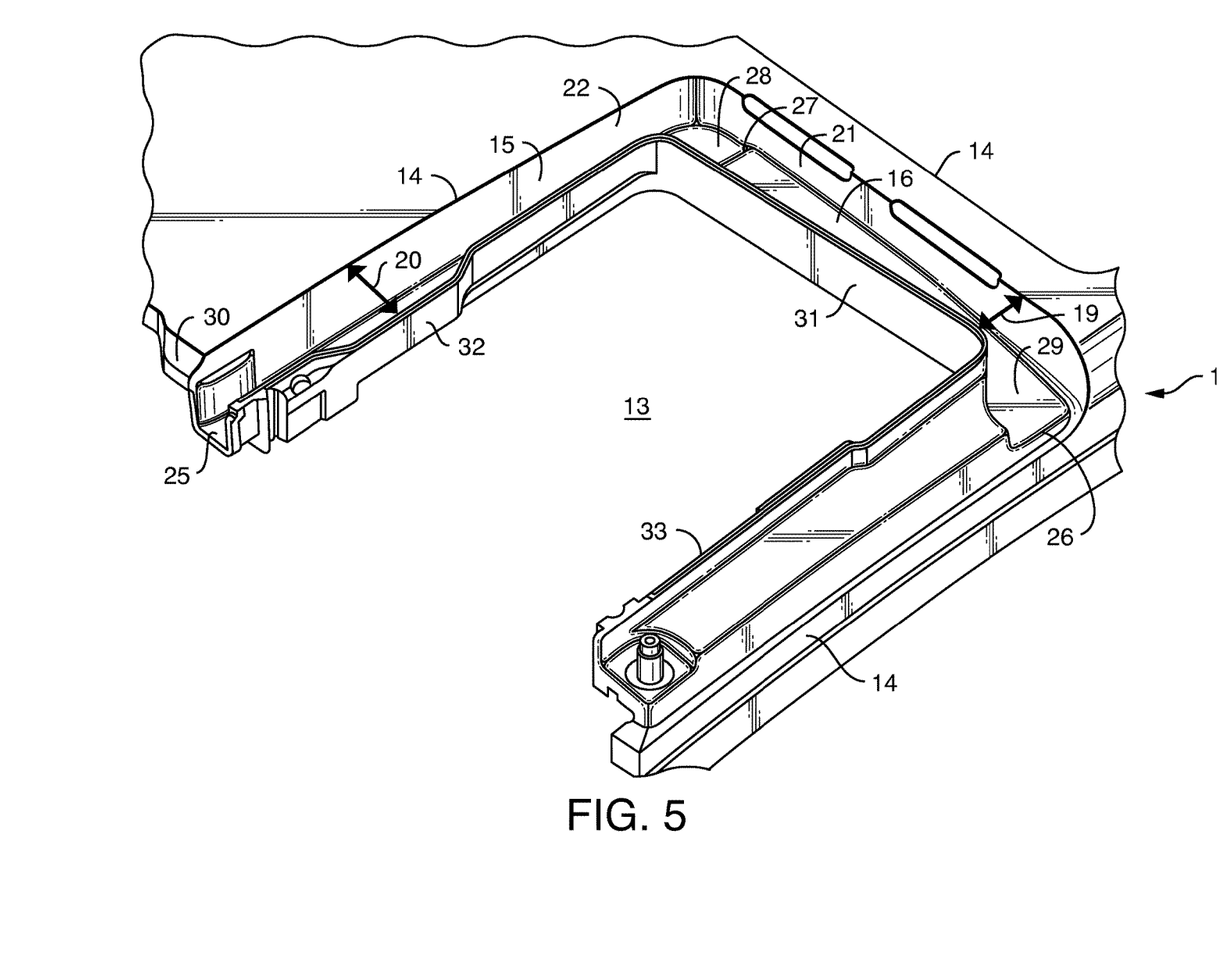
FIG. 5 is a perspective view of a section of the housing of FIG. 1 to be covered with the first cover of FIG. 4.

As is best seen in FIG. 5, the housing 1 has a first opening 13 on its top side to be closed by the first cover 2. In an edge area 14 of the first opening 13 are arranged two mounting grooves 15, 16, whereby one mounting groove 15 comes to lie below the two collars 7, 11 and the other mounting groove 16 comes to lie below the two collars 6, 10. As is best seen in FIG. 4, the two collars 6, 10 lie at a distance 17 to one another, whereby the distance 17 varies over the course of the two collars 6, 10. The same applies to the distance 18 between the two collars 7 and 11. The widths 19, 20 of the two mounting grooves 16 and 15 vary corresponding to the distances 17, 18, as can be seen in FIG. 5. Between the outside of the outer collar 6, 7 and of the opposing wall 21, 22 of the respective mounting groove 16, 15 remains a gap 23, 24 each with a width von 2 mm, through which liquid poured possibly onto the top side of the housing 1 can penetrate in order to reach the respective mounting groove 15, 16.

The mounting groove 15 has an end 25, which is best seen in FIG. 5. The mounting groove 16 has an end 26 as well. In the boundary area between the two mounting grooves 15, 16, there is a highest point 27. Starting from the highest point 27 the bottom 28 of the mounting groove 15 as well as the bottom 29 of the mounting groove 16 are inclined in the direction of the respective end 25, 26. Because of the incline of the two bottoms 28, 29, the liquid collected in the mounting groove 15 will run in the direction of end 25, while the liquid reaching the mounting groove 16 flows in the direction of the end 26 and exits at the respective end 25, 26 from the housing 1. As is seen in FIG. 5, the end 25 projects somewhat over the associated housing wall 30, such that the liquid exiting there may drip at a distance to the housing 1.

The mounting grooves 15, 16 are designed with a depth between 15 mm and 25 mm and a width between 15 mm and 30 mm as well as a corresponding length, such that they can receive a liquid volume of more than 100 mL without the liquid splashing over the inner walls 31, 32 and might penetrate the interior of the housing 1 through the housing opening 13. Furthermore, the inside of the inner collar 9, 10, 11 of the cover lies at a distance 34 from the respective inner wall 31, 32, 33 of the housing 1, such that an adherence of liquid between the inner wall 31, 32, 33 of the mounting groove 15, 16 and the inside of the inner collar 9, 10, 11 is prevented.

The upper edge of the inner wall 31, 32, 33 of the mounting grooves 15, 16 lie each higher than the lower edge of 12 of the collar 5, 6, 7 of the cover 2 in order to prevent splashing through of liquid flowing in a flood-like pattern into the opening 13 of the housing 1.

Figure 2:
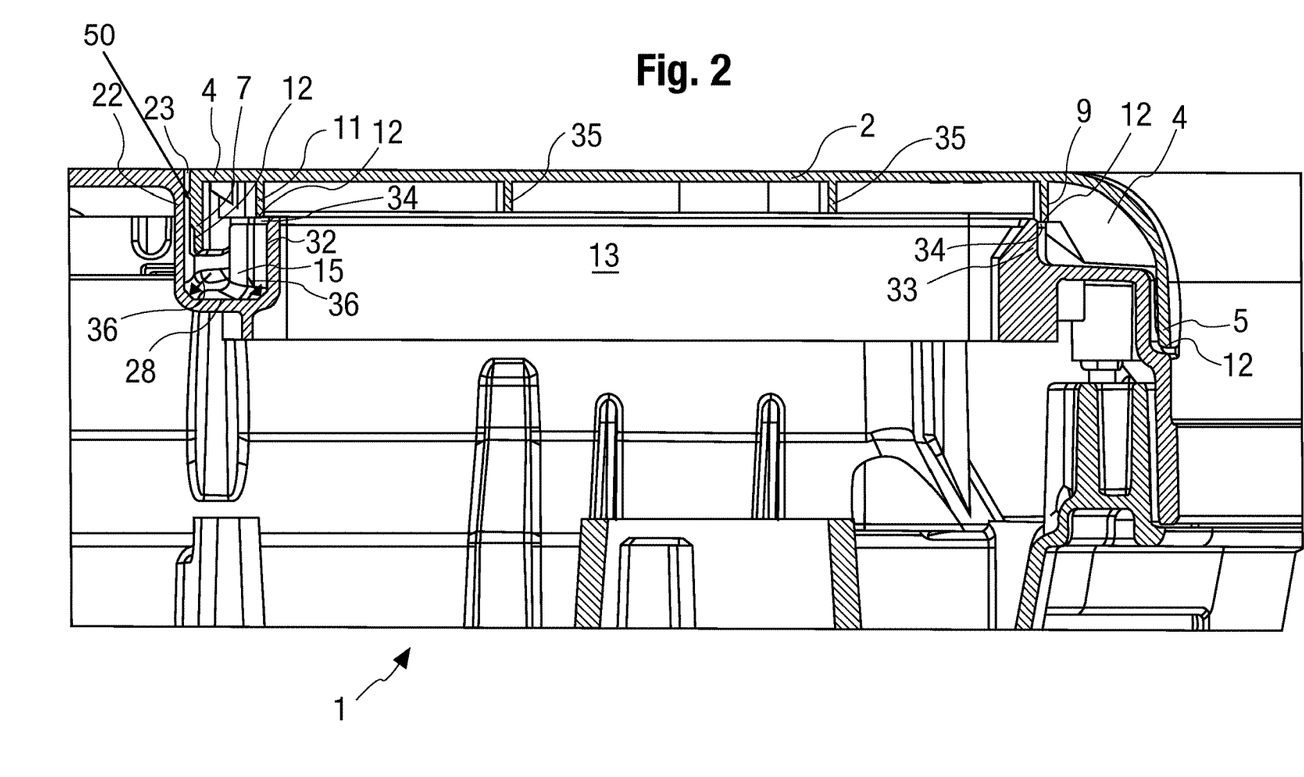
FIG. 2 is a section through the housing according to a line B-B of FIG. 1.
Figure 3:
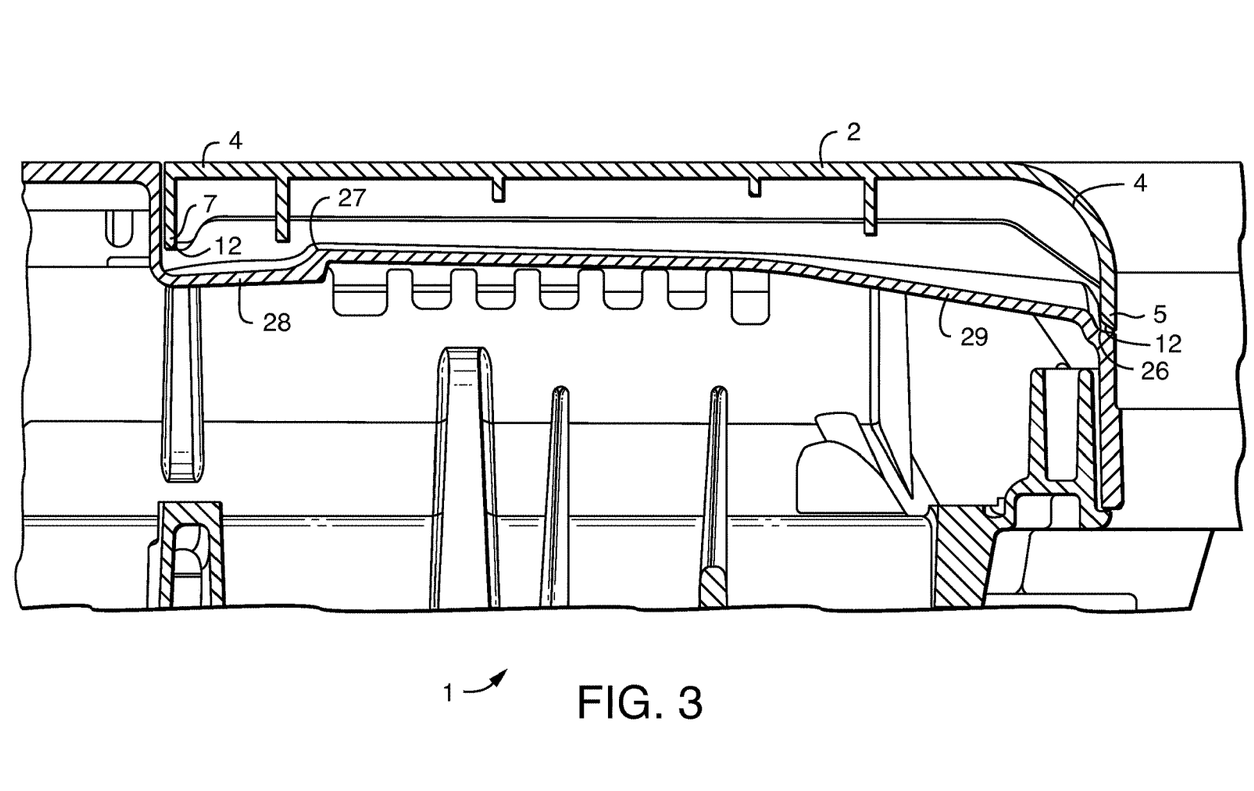
FIG. 3 is a section through the housing according to a line A-A of FIG. 1.

As is best seen in FIG. 2, the cover 2 lies on the upper edge of the inner wall 31, 32, 33 of the mounting groove 15, 16 by means of bars 35 mounted on its bottom side.

As is best seen in FIG. 2, the inner radii 36 of the mounting grooves 15, 16 are designed as greater than 3 mm, such that the mounting grooves 15, 16 can be cleaned in a simple manner without the aid of special tools.

Figure 6:
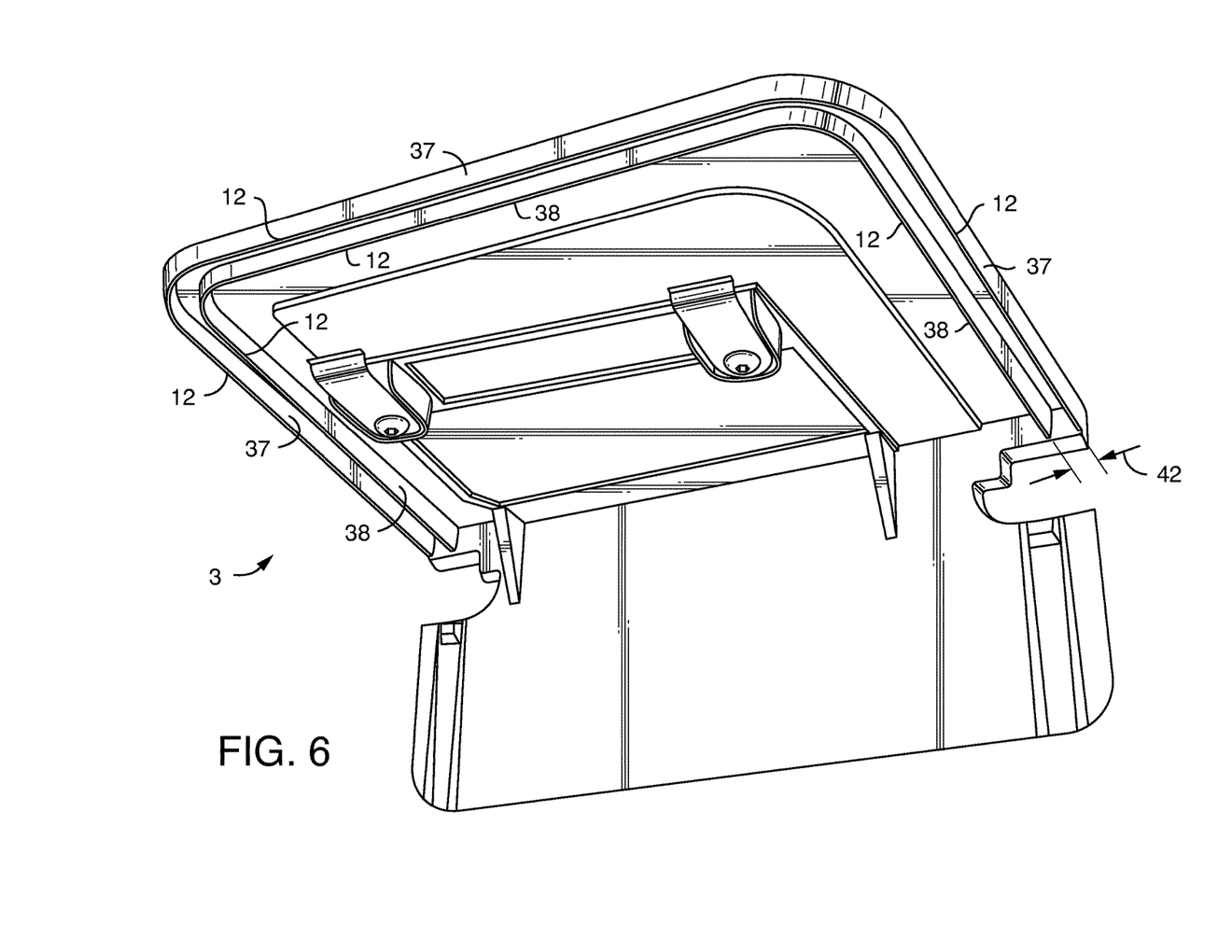
FIG. 6 is a perspective view of the bottom side of a second cover of the housing of FIG. 1.
Figure 7:
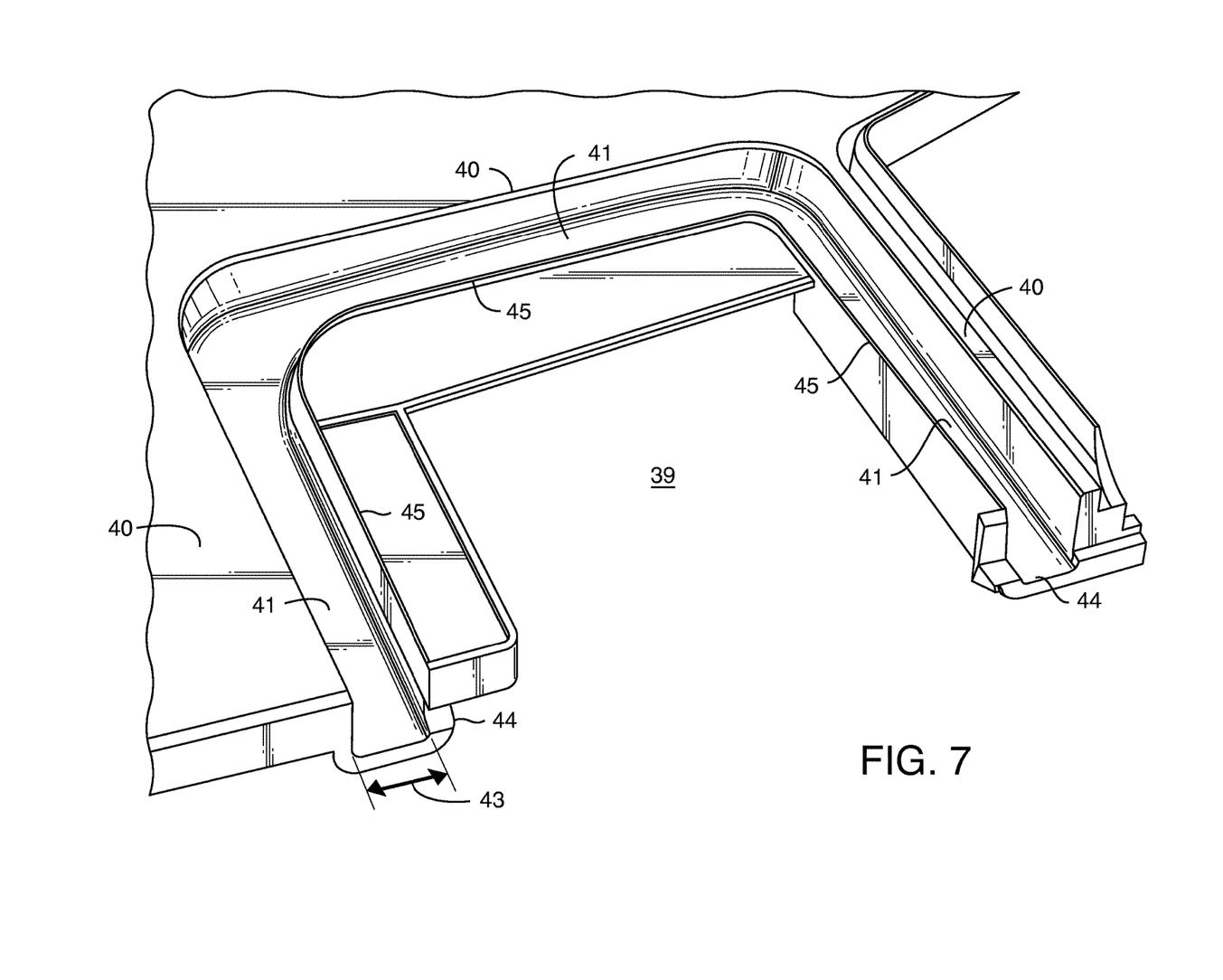
FIG. 7 is a perspective view of an area of the housing of FIG. 1 to be covered with the cover of FIG. 6.

Corresponding to the larger, first cover, the second, smaller cover 3 is designed with an outer collar 37 and an inner collar 38, which have a drip edge 12 each. The second cover 3 is provided for closing a second, smaller opening 39 of the housing 1. The edge area 40 of the second opening 39 is provided with a three-part mounting groove 41, into which the two collars 37, 38 protrude from above downwards at a distance 42 to one another. Regarding the width 43 of the mounting groove 41 and the distance to the outside of the outer collar 37, through which a (cannot be seen here) gap forms, as well as regarding the distance between the inner collar 38 and the inner wall 45 of the mounting groove 41, the same applies to the second exemplary embodiment with the second cover 3 as was described in connection with the first cover 2. Also regarding the downward inclination of the mounting groove 21 from its center towards the two ends 44, the same applies as in the first exemplary embodiment.

While specific embodiments of the invention have been shown and described in detail to illustrate the application of the principles of the invention, it will be understood that the invention may be embodied otherwise without departing from such principles.

APPENDIX
LIST OF REFERENCE NUMBERS

| | | | |
|---|---|---|---|
| 1 | Housing | 26 | End |
| 2 | First, larger cover | 27 | Highest point |
| 3 | Second, smaller cover | 28 | Bottom |
| 4 | Outer edge area | 29 | Bottom |
| 5-8 | Outer collar | 30 | Housing wall |
| 9-11 | Inner collar | 31 | Inner wall |
| 12 | Drip edge | 32 | Inner wall |
| 13 | First opening # | 33 | Inner wall |
| 14 | Edge area | 34 | Distance |
| 15 | Mounting groove | 35 | Bars |
| 16 | Mounting groove | 36 | Inner radii |
| 17 | Distance | 37 | Outer collar |
| 18 | Distance | 38 | Inner collar |
| 19 | Width | 39 | Second opening |
| 20 | Width | 40 | Edge area |
| 21 | Wall | 41 | Mounting groove |
| 22 | Wall | 42 | Distance |
| 23 | Gap | 43 | Width |
| 24 | Gap | 44 | End |
| 25 | End | 45 | Inner wall |

What is claimed is:

1. A device housing for devices with at least one module, which is to be protected against penetration of liquids, the device housing comprising:

a housing with a top side opening having an edge area comprising at least one mounting groove, said housing comprising a first wall and a second wall, at least said first wall and said second wall defining said mounting groove, wherein at least one outlet is provided for each said mounting groove through which penetrated liquid is guided out of the housing;

a cover arranged on the top side of the housing closing the opening in a closed position, the cover having an outer edge area comprising a collar which protrudes downwards when the cover is in the closed position and having a drip edge arranged below the collar when the cover is in the closed position, such that a liquid dripping from the drip edge falls into the mounting groove, wherein the cover has another collar to provide two collars arranged at a distance to one another, each of said two collars protruding downwards into the mounting groove, said collar and said another collar being directly connected to the same cover, wherein at least a portion of each of said two collars is located between said first wall and said second wall.

2. A housing in accordance with claim 1, wherein a gap is formed between an outside of said housing and one of said two collars and the housing has a gap width, at which an adherence of liquid is prevented as a result of capillary forces, one of said first wall and said second wall and said one of said two collars defining said gap, said collar being parallel to said another collar.

3. A housing in accordance with claim 2, wherein the gap has a gap width of more than 1 mm and at most 4 mm.

4. A housing in accordance with claim 1, wherein the mounting groove has at least one end through which penetrated liquid is guided out of the housing, said at least one end being located at or adjacent to said at least one outlet, wherein said first wall and said second wall terminate at said at least one end, said edge area comprising an outermost edge of said cover, said one collar being located between said outermost edge and said another collar.

5. A housing in accordance with claim 4, wherein the end projects laterally over a housing wall, said housing comprising said at least one outlet and another outlet to provide two outlets, said at least one outlet being located at a spaced location from said another outlet, said one collar being located adjacent to one of said first wall and said second wall when the cover is in the closed position, said another collar being located adjacent to another one of said first wall and said second wall when the cover is in the closed position.

6. A housing in accordance with claim 4, wherein the mounting groove is inclined towards the end.

7. A housing in accordance with claim 1, wherein the mounting groove has a liquid volume capacity of at least 100 mL, without liquid reaching the modules to be protected in an interior of the housing.

8. A housing in accordance with claim 1, wherein one of said first wall and said second wall is an inner wall, the mounting groove having said inner wall lying below the closed cover, said two collars being spaced from said inner wall such that an adherence of liquid between the inner wall of the mounting groove and the inside of the two collars is prevented as a result of capillary forces.

9. A housing in accordance with claim 8, wherein an upper edge of the inner wall of the mounting groove is higher than a lower edge of the two collars of the cover.

10. A housing in accordance with claim 9, wherein the cover lies on an upper edge of the inner wall of the mounting groove.

11. A housing in accordance with claim 1, wherein the mounting groove has a rounded profile with an inner radius.

12. A housing in accordance with claim 11, wherein the inner radii of the mounting groove are greater than 3 mm.

13. A housing in accordance with claim 1, wherein the depth of the mounting groove is greater than 5 mm and its width is greater than 10 mm.

14. A medical device housing, which medical device is to be protected against penetration of liquids, the medical device housing comprising:
- a housing wall with an opening having an edge area comprising a mounting groove;
- another housing wall arranged opposite said housing wall, at least said housing wall and said another housing wall defining said mounting groove, said housing wall and said another housing wall terminating at an end of said mounting groove that drains liquid;
- a removable cover closing the opening in a cover closed position, the cover having an outer edge area comprising an outer edge surface and a collar which protrudes downwards when the cover is in the cover closed position and having a drip edge at a bottom of the collar when the cover is in the cover closed position, such that a liquid dripping from the drip edge falls into the mounting groove, wherein the cover has another collar to provide two collars arranged at a distance to one another, each collar protruding downwards into the mounting groove, said collar being arranged between said outer edge surface and said another collar.

15. A medical device housing in accordance with claim 14, wherein:
- a gap is formed between an outside of one of the collar and said another collar and the another housing wall, said gap having a gap width, at which an adherence of liquid is prevented as a result of capillary forces;
- said collar is located between said another collar and one of said housing wall and said another housing wall when the cover is in the cover closed position, said another collar being located between said collar and another one of said housing wall and said another housing wall when the cover is in the cover closed position; and
- said collar extends parallel to said another collar.

16. A medical device housing in accordance with claim 15, wherein the gap has a gap width of about 2 mm.

17. A medical device housing in accordance with claim 14, wherein the mounting groove has a liquid volume capacity of more than 200 mL, whereby less than 200 mL of liquid will not reach the medical device in an interior of the housing, said collar being located adjacent to said one of said housing wall and said another housing wall when the cover is in the cover closed position, said another collar being located adjacent to said another one of said housing wall and said another housing wall when the cover is in the cover closed position.

18. A medical device housing in accordance with claim 14, wherein the inner radii or inner radius of the mounting groove are or is greater than 5 mm.

19. A device housing for devices with at least one module, which is to be protected against penetration of liquids, the device housing comprising:
- a housing with a top side opening having an edge area comprising a mounting groove, said housing comprising a first housing wall, a second housing wall and a housing portion extending between said first housing wall and said second housing wall, said first housing wall defining said top side opening, said first wall, said second wall and said housing portion defining said mounting groove;
- a cover arranged on the top side of the housing closing the opening in a cover closed position, the cover having an outer edge area comprising an outer edge, a first collar and a second collar, said first collar being arranged at a spaced location from said second collar, said first collar being parallel to said second collar, said second collar being arranged inwardly of said first collar and said outer edge in a direction of an interior of said cover, wherein said first collar and said second collar are directly connected to the same cover, each of said first collar and said second collar having a drip edge, said drip edge of said first collar and said drip edge of said second collar extending downward from said cover into said mounting groove when the cover is in the cover closed position, wherein said drip edge of said first collar and said drip edge of said second collar are arranged in said mounting groove when the cover is in the cover closed position, such that a liquid dripping from the drip edge of said first collar and the drip edge of said second collar falls into the mounting groove.

20. A device in accordance with claim 19, wherein one of said first collar and said second collar is an outer collar and another one of said first collar and said second collar is an inner collar, said outer collar and said second housing wall defining a gap, said gap being in communication with said mounting groove, said housing portion defining a bottom of said mounting groove, said drip edge of said first collar and said drip edge of said second collar being arranged between said first housing wall and said second housing wall, said inner collar being located at a spaced location from said first housing wall, said housing comprising an outlet, said first housing wall and said second housing wall having an end portion located at said outlet, said first collar being located between said outer edge and said second collar, said first collar being located adjacent to one of said first housing wall and said second housing wall when the cover is in the closed position, said second collar being located adjacent to another one of said first housing wall and said second housing wall when the cover is in the closed position.

* * * * *